United States Patent [19]

Weber

[11] 4,447,915

[45] May 15, 1984

[54] EXPANDABLE MEDULLARY CANAL PLUG

[75] Inventor: Bernhard G. Weber, St. Gallen, Switzerland

[73] Assignee: Sulzer Brothers Limited, Winterthur, Switzerland

[21] Appl. No.: 345,380

[22] Filed: Feb. 3, 1982

[30] Foreign Application Priority Data

Feb. 18, 1981 [CH] Switzerland ............... 1064/81

[51] Int. Cl.³ ............................................. A61F 1/04
[52] U.S. Cl. .................................... 3/1.9; 128/92 C
[58] Field of Search ............... 3/1.9, 1.91, 1, 1.912; 128/92 B, 92 C

[56] References Cited

U.S. PATENT DOCUMENTS

| | | | |
|---|---|---|---|
| 3,924,275 | 12/1975 | Heimke | 128/92 C X |
| 4,011,602 | 3/1977 | Rybicki et al. | 3/1.9 |

FOREIGN PATENT DOCUMENTS

| | | | |
|---|---|---|---|
| 6408 | 1/1980 | European Pat. Off. | 3/1.9 |
| 2359644 | 7/1975 | Fed. Rep. of Germany | 128/92 B |
| 2945628 | 5/1981 | Fed. Rep. of Germany | 128/92 B |

*Primary Examiner*—Richard J. Apley
*Assistant Examiner*—David J. Isabella
*Attorney, Agent, or Firm*—Kenyon & Kenyon

[57] ABSTRACT

The medullary canal plug is formed by a deformable and expandable outer body having a jacket formed of a number of segments and a conical expansion body which is pulled into the outer body in order to expand the outer body. Spreading of the outer body causes barb-like anchoring elements to hook into the inner wall of a bone. The two bodies are permanently secured together via serrations on the inside of the outer body and the outside of the expansion body.

14 Claims, 5 Drawing Figures

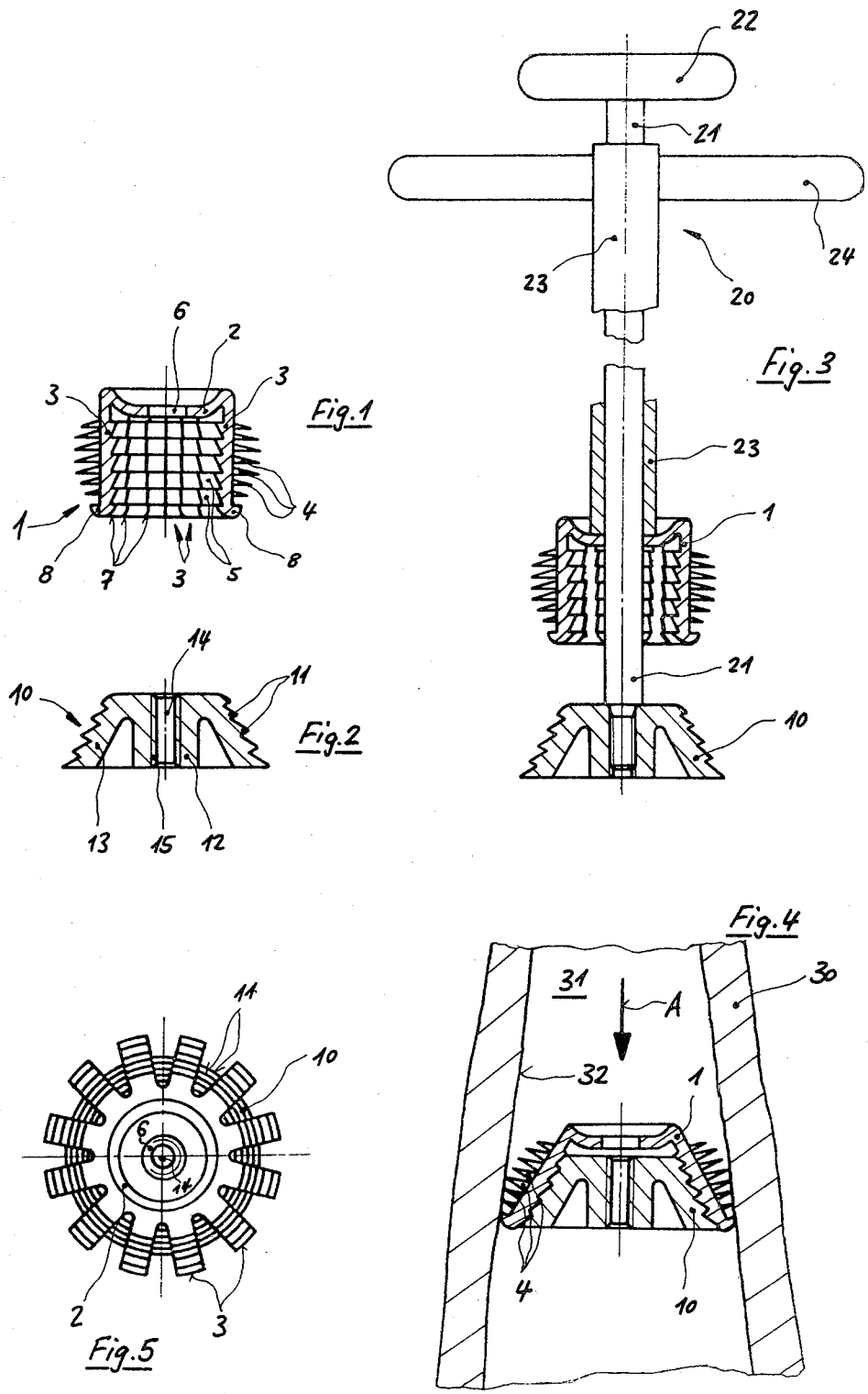

EXPANDABLE MEDULLARY CANAL PLUG

This invention relates to an expandable medullary canal plug. More particularly, this invention relates to a plug which can be placed in a widening medullary canal of a tubular bone.

As is known, when an endoprothesis is to be anchored in a bone by means of a bone cement, the cement is first introduced into an operatively prepared opening in the bone and, thereafter, a shank of the prothesis is pressed or knocked into the cement. In some cases, it has been necessary to prevent the axial displacement of the bone cement in the bone opening. This is usually accomplished with the use of a plug. Generally, the plugs which have been used to prevent axial flow of the bone cement have had various shapes and forms. For example, as described in U.S. Pat. No. 4,245,359, one known plug is formed with a plurality of spaced coaxial rings, each of which is formed with radially directed elastically deformable flanges. During insertion, the flanges are bent along the wall of the medullary canal in the style of a calyx to form a stopper-type closure for the medullary canal section in which an endoprosthesis is to be anchored. Once the plug is in place, the bone cement which is subsequently filled into the canal cannot drain past the plug as the prothesis shank is driven in. Instead, the cement is displaced laterally against the wall of the medullary canal as much as possible.

One prerequisite for a strong adhesion of the known plugs on the lateral walls of a tubular bone is that the medullary canal of the bone must narrow or, at least, does not widen. However, this is not always the case. For example, the medullary canal of the femur is of hourglass shape. That is, the canal widens from the center upward as well toward the distal end of the femur. Therefore, when a femur head prosthesis with an extended anchoring shank is inserted at the proximal end of a femur, it may be necessary to insert a stopper-type plug into the widened region of the medullary canal from the proximal side by passing beyond the center of the bone having the narrowest canal cross-section. In such cases, if the plug is of a rigid type, the outer dimensions of the plug may not be sufficient to achieve a firm fit. In the case of a plug with elastically deformable flanges, the flanges may be deformed to the extent that a firm fit cannot be obtained.

Accordingly, it is object of the invention to provide a suitable medullary canal plug for a medullary canal which widens inwardly at an intermediate section.

It is another object of the invention to provide a medullary canal plug which can be readily adapted to changes in dimension of a medullary canal.

It is another object of the invention to provide for an effective anchoring of an endoprothesis shank within a bone having a widening canal.

Briefly, the invention provides a plug comprised of a one-piece hood-shaped expandable body and a one-piece expansion body. The expandable body has a base, a plurality of segments which extend from the base in the form of a segmented jacket to define an interal cavity and a plurality of anchoring elements on the exterior surface of each segment. The expansion body is sized to fit into the cavity of the expandable body and to move the segments outwardly in order to expand the expandable body. In addition, means are provided for fixing the expansion body in the expandable body. Also, each body can be made of a material which is elastically deformable.

The construction of the plug is such that the expandable body and expansion body can be introduced successively through a relatively narrow operative opening into a bone and can be fixed in a widened part of the canal by drawing the expansion body into the internal cavity of the expandable body. Alternatively, the two bodies can be jointly threaded onto an instrument for insertion and placement in a bone canal.

The means for fixing the expansion body in the expandable body may include at least one serration within the cavity of the expandable body and at least one serration on the expansion body. These serrations may be directed in opposite directions to each other. If at least one of the two bodies is provided with progressive tooth rows, one behind the other in the axial direction, a stepwise spreading of the expandable body can be obtained.

The threading up of the two bodies of the plug and the drawing in of the expansion body into the expandable body can be simplified if the bottom of the expandable body and the expansion body have central coaxial bores and if means are provided in the bore of the expansion body for detachably engaging a pulling instrument. In this way, the bodies can be mounted on the pulling instrument for implantation in an operatively prepared medullary canal.

FIG. 1 illustrates an axial longitudinal sectional view of an expandable body constructed in accordance with the invention in a closed state;

FIG. 2 illustrates an axial longitudinal section of an expansion body constructed in accordance with the invention;

FIG. 3 illustrates the bodies of FIGS. 1 and 2 mounted on a pulling instrument in accordance with the invention;

FIG. 4 illustrates a longitudinal sectional view through a tubular bone with a plug according to the invention in place; and FIG. 5 illustrates a view taken in the direction of arrow A of FIG. 4 with the bone being omitted.

Referring to FIGS. 1 and 2, the medullary canal plug is composed of an outer expandable body 1 and a conical expansion body 10.

Referring to FIG. 1, the outer body 1 is formed of one-piece in a hood or cup shape. In the closed state shown, the body is in the form of an inverted cup of substantially uniform diameter. In addition, the body 1 has a base 2 which is slightly depressed and which is relatively easy to deform plastically or elastically. Also, the body 1 has a plurality of segments 3 which extend from the base 2 to define a segmented jacket which, in turn, defines an internal cavity. The segments 3 can be formed by dividing cuts 7 which extend through the jacket into the region of the bottom 2.

As indicated, each of the segments 3 has a plurality of barb-like anchoring elements 4 on the exterior surface. These anchoring elements 4 are distributed over the height of the jacket to form several rows. The elements 4 are originally formed, that is, before the jacket is divided, for example, as circular ribs which become sectioned by the cuts 7. As shown in FIG. 1, the anchoring elements 4 define an outer contour with intermediate anchoring elements being of greater length than the anchoring elements near the respective ends of the outer body.

The free edge of the body 1 terminates in a shoulder 8 which is rounded externally for easier introduction into a bone or for easier drawing in of the expansion body 10. The shoulder 8 may also form a barb.

In addition, the body 1 is provided with rows of serrations 5 within the cavity while the bottom 2 is provided with a central coaxial bore 6.

Referring to FIG. 2, the expansion body 10 is of conical shape and is sized for movement into the cavity of the outer body 1 in order to spread the segments 3 radially outwardly of the base 2 as indicated in FIG. 5. As indicated, the expansion body 10 has a central stem 12 and an elastically deformable peripheral wall 13 spaced from and about the stem 12 in the manner of an umbrella. On being introduced into a bone through a relatively narrow operative opening, the peripheral wall 13 is compressed elastically, for example, to the size of its smallest diameter.

The expansion body 10 also has a plurality of rows of serrations 11 on the outer surface for engaging with the serrations 5 of the outer body 1. In addition, the body 10 has a central coaxial bore 14 in which a thread 15 is provided.

The serrations 5, 11 on the respective bodies 1, 10 provide a means for fixing the expansion body 10 in the outer body 1 in a non-detachable manner. To this end, the serrations 5, 11 are oppositely directed to each other.

Referring to FIG. 3, in order to introduce the bodies 1, 10 of the plug into a bone, use can be made of an introducing and pulling instrument. As indicated, such an instrument includes a spindle 21 having a main portion on which the outer body 1 can be slidably mounted as well as a reduced threaded end portion which is threaded into the bore 14 of the expansion body 10. The instrument 20 is of a length which is adapted to the maximum depth at which the medullary canal plug must be introduced into the bone. In addition, the instrument carries a handle 22 at the outer end. In addition, a tube 25 is slidably mounted over the spindle 21 to provide an abutment for the bottom 2 of the outer body 1. This tube 25 is provided with a second larger handle 24 at the upper end below the handle 22 of the spindle 21.

When the instrument is used, the outer body 1 is slid onto the spindle 21 before the expansion body 10 is threaded on. In this case, the bore 6 of the outer body 1 is adapted to the cross-section of the spindle 21 in such a way that the closed outer body 1 adheres to the spindle 21 by friction for introduction into the bone. Alternatively, the outer body 1 may be supported by the expansion body 10 screwed on the spindle 21 in order to slightly increase the adherence of the outer body 1 on the spindle 21.

It is known that in a femur, the narrowest point of the medullary cavity lies approximately in the center. Hence, the canal towards the condyles. Referring to FIG. 4, the section of the femur bone 30 shown schematically represents the section lying beyond the middle of the femur as viewed from the femur head (not shown). This section of bone 30 also indicates the widening portion of the canal below the mid-point of the bone. In order to insert a very long shank of a hip joint protheses, as is necessary, for example, in a re-operation prothesis, a cut-out 31 widening in the direction indicated by the arrow A must be operatively created in the medullary canal. In such cases, the plug is mounted in the widened cut-out in order to close off the canal toward the downwardly contiguous condyles (not shown).

In order to mount the bodies 1, 10 of the plug in the bone 30, the bodies 1, 10 are mounted on the instrument 20 as shown in FIG. 3. The instrument 20 with the bodies thereon is then inserted into the bone 30, possibly after compression of the elastic expansion body 10. Introduction is from above through the relatively narrow operative opening (not shown). The position in which the outer body 1 is at the point of the cut-out 31 intended for the location of the plug may be indicated on the tube 23 by a marking. Such a marking may indicate the depth necessary below the operative opening. After the correct position for the outer body 1 has been reached, the spindle 21 is pulled upward by means of the handle 22 relative to the tube 23. This causes the expansion body 10 to slide into the cavity of the closed outer body 1. Since the outer body 1 is hindered from yielding upwardly by abutting against the lower end of the tube 23, the segments 3 of the outer body 1 begin to expand. As the expansion body 10 penetrates further into the outer body 1, the individual segments 3 are pushed apart to all sides with the anchoring elements 4 hooking into the rough surfaces of the inner wall 32 of the cortical bone tissue. At the same time, the expansion body 10 closes the spaces created between the opened segments 3 during expansion as can be seen in FIG. 5.

Once in place, a permanent connection is formed between the expanded outer body 1 and the expansion body 10 by virtue of the fact that the serrations 5, 11 interengage with each other.

The preferred materials for the individual bodies 1, 10 of the plug are the biologically compatible and biologically stable plastics normally used in implant procedures. In particular, polyethylene of the classifications HDPE and UHMW can be used. However, it is also possible to make the individual bodies 1, 10 of one of the metals or metal alloys customary for endoprotheses.

In order to be able to close medullary canals of greatly different diameters, it may be expedient to have outer bodies and expansion bodies of different diameters at hand as a type series. For example, medullary canal diameters of from 10 to 35 millimeters can be closed with three different sizes.

Of note, various techniques and instruments may be used for mounting the medullary canal plug other than those described above.

The invention thus provides a medullary canal plug which can be placed in widening sections of a bone in a secure manner. Further, once in place, the individual components of the plug are permanently connected to each other so as to resist loosening within the bone.

What is claimed is:

1. A medullary canal plug comprising
a cup-shaped outer body having a base and segmental jacket defining an internal cavity and including at least two segments extending from said base with a plurality of externally disposed deformable anchoring elements on said segments;
a conical expansion body for movement into said cavity of said outer body to spread said segments radially outwardly of said base; and
means for fixing said expansion body within said cavity of said outer body.

2. A medullary canal plug as set forth in claim 1 wherein said means includes a plurality of serrations on an inner wall of said cavity of said outer body and a plurality of serrations on said expansion body for engaging with said serrations of said outer body.

3. A medullary canal plug as set forth in claim 1 wherein said expansion body is elastically deformable to be compressed for passage through a narrow operative opening in a bone.

4. A medullary canal plug as set forth in claim 1 wherein each body has a central bore coaxial of the bore of the other body.

5. A medullary canal plug as set forth in claim 4 wherein said expansion body has means in said bore thereof for detachably engaging a pulling instrument.

6. A medullary canal plug comprising
a one-piece cup-shaped expandable body having a base, a plurality of segments extending from said base to define an internal cavity and a plurality of anchoring elements on an exterior surface of each segment;
a one-piece expansion body sized to fit into said cavity and to move said segments outwardly to expand said expandable body, said expansion body including a stem and an elastically deformable peripheral wall spaced from and about said stem; and
means for fixing said expansion body in said expandable body.

7. A medullary canal plug as set forth in claim 6 wherein each said body is elastically deformable to facilitate expansion of said expandable body and to permit passage of said expansion body through a narrow opening in a bone.

8. A medullary canal plug as set forth in claim 6 wherein said means includes at least one serration on said expandable body within said cavity and at least one serration on said expansion body for engaging with said serration of said expandable body.

9. A medullary canal plug as set forth in claim 6 wherein each body has a central bore coaxial of the bore of the other body for passage of a pulling instrument.

10. A medullary canal plug comprising
a cup-shaped outer body having a base and a segmental jacket defining an internal cavity and including at least two segments and a plurality of external barb-like anchoring elements disposed in rows on said segments;
a conical expansion body for movement into said cavity of said outer body to spread said segments radially outwardly of said base; and
means for fixing said expansion body within said cavity of said outer body.

11. A medullary canal plug as set forth in claim 10 wherein said anchoring elements define an outer contour with intermediate anchoring elements being of greater length than than the anchoring elements near the respective ends of said outer body.

12. A medullary canal plug as set forth in claim 11 wherein said outer body is elastically deformable to be compressed for passage through a narrow opening in a bone.

13. A medullary canal plug as set forth in claim 10 wherein said outer body is of uniform diameter with a free edge terminating in a shoulder.

14. A medullary canal plug comprising
a cup-shaped outer body having a base and segmental jacket defining an internal cavity and including at least two segments and a plurality of external barb-like anchoring elements disposed in rows on said segments, said anchoring elements defining an outer contour with intermediate anchoring elements being of greater length than the anchoring elements near the respective ends of said outer body;
a conical expansion body for movement into said cavity of said outer body to spread said segments radially outwardly of said base; and
means for fixing said expansion body within said cavity of said outer body.

* * * * *